(12) United States Patent
Tsoukalis

(10) Patent No.: US 8,475,409 B2
(45) Date of Patent: Jul. 2, 2013

(54) INFUSION PUMP

(75) Inventor: Achilleas Tsoukalis, Anavyssos (GR)

(73) Assignee: Micrel Medical Devices S.A., Gerakas (GR)

( * ) Notice: Subject to any disclaimer, the term of this patent is extended or adjusted under 35 U.S.C. 154(b) by 134 days.

(21) Appl. No.: 12/832,259

(22) Filed: Jul. 8, 2010

(65) Prior Publication Data

US 2011/0009814 A1 Jan. 13, 2011

(30) Foreign Application Priority Data

Jul. 8, 2009 (GR) .................................. 090100384

(51) Int. Cl.
*A61M 5/20* (2006.01)

(52) U.S. Cl.
USPC .............................. 604/134; 604/131; 604/66

(58) Field of Classification Search
USPC ......... 604/65–67, 29, 131–134, 141; 600/365
See application file for complete search history.

(56) References Cited

U.S. PATENT DOCUMENTS

| | | | |
|---|---|---|---|
| 5,049,141 A | 9/1991 | Olive | |
| 5,609,572 A | 3/1997 | Lang | |
| 5,980,490 A | 11/1999 | Tsoukalis | |
| 6,659,980 B2 | 12/2003 | Moberg et al. | |
| 6,699,218 B2 | 3/2004 | Flaherty et al. | |
| 6,740,072 B2 | 5/2004 | Starkweather et al. | |
| 6,749,587 B2 * | 6/2004 | Flaherty | 604/151 |
| 6,762,210 B1 | 7/2004 | Oguro et al. | |
| 6,948,918 B2 * | 9/2005 | Hansen | 417/395 |
| 6,960,864 B2 | 11/2005 | Urano et al. | |
| 7,144,384 B2 | 12/2006 | Gorman et al. | |
| 7,150,741 B2 | 12/2006 | Erickson et al. | |
| 7,161,484 B2 | 1/2007 | Tsoukalis | |

(Continued)

FOREIGN PATENT DOCUMENTS

| | | |
|---|---|---|
| DE | 102005058080 A1 | 6/2007 |
| EP | 1410814 A2 | 4/2004 |

(Continued)

OTHER PUBLICATIONS

Greek Patent Office; Greek Search Report datedJul. 16, 2010; pp. 1-7.

*Primary Examiner* — Laura A Bouchelle
*Assistant Examiner* — Melissa A Snyder
(74) *Attorney, Agent, or Firm* — Duane Morris LLP; Rodman Steele, Jr.; Gregory M. Lefkowitz

(57) ABSTRACT

Described is an infusion pump comprising electronic infusion regulating means with wired or wireless communication means and a power source, a medicament bag (7) and an infusion device, said infusion device being in fluid communication with said medicament bag (7) and comprising two valves (1, 2), a pressure cavity (4) provided between said two valves (1, 2) and a membrane (3) covering said cavity (4), wherein said infusion device comprises at least two active actuators, preferably either made of electroactive polymer so as to form a self actuating membrane (3) or made of shape memory alloy wire, one of said actuators being adapted to apply pressure to said membrane (3) for fluid displacement in said cavity (4), and the other of said actuators being adapted to operate one of said valves which is adapted to passively close in the flow direction of a fluid from said medicament bag (7) through the cavity (4), wherein the other of said valves is adapted to, in particular passively, close in a direction opposite to said flow direction.

20 Claims, 3 Drawing Sheets

U.S. PATENT DOCUMENTS

| | | |
|---|---|---|
| 7,307,166 B1 | 12/2007 | Von Borstel et al. |
| 7,353,747 B2 | 4/2008 | Swayze et al. |
| 7,371,223 B2 | 5/2008 | Couvillon, Jr. et al. |
| 7,521,840 B2 | 4/2009 | Heim |
| 2002/0169439 A1 | 11/2002 | Flaherty |
| 2003/0117044 A1 | 6/2003 | Urano et al. |
| 2004/0115068 A1 | 6/2004 | Hansen et al. |
| 2007/0179434 A1* | 8/2007 | Weinert et al. ............... 604/66 |
| 2008/0038128 A1* | 2/2008 | Haar ............................ 417/474 |
| 2010/0228110 A1 | 9/2010 | Tsoukalis |
| 2011/0166524 A1 | 7/2011 | Preuthun et al. |

FOREIGN PATENT DOCUMENTS

| | | |
|---|---|---|
| EP | 1695727 A2 | 8/2006 |
| EP | 1818664 A1 | 8/2007 |
| JP | 2007127086 A | 5/2007 |
| WO | 9117780 A1 | 11/1991 |
| WO | 9625189 A1 | 8/1996 |
| WO | 2006108775 A2 | 10/2006 |
| WO | 2008079440 A2 | 7/2008 |

* cited by examiner

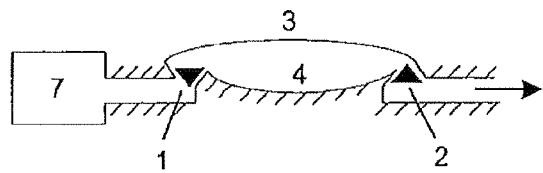
Fig.1 (prior art)
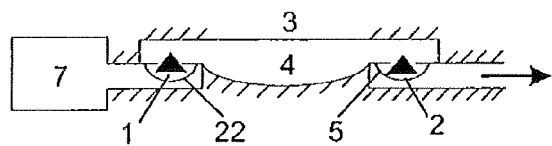
Fig.2a
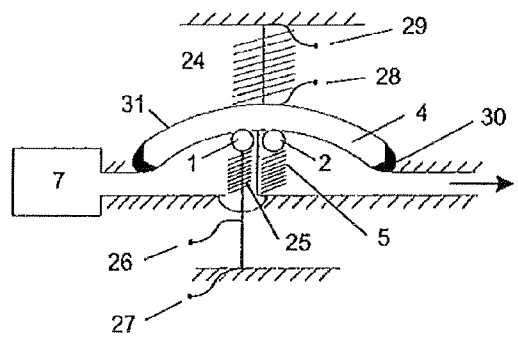
Fig.2b
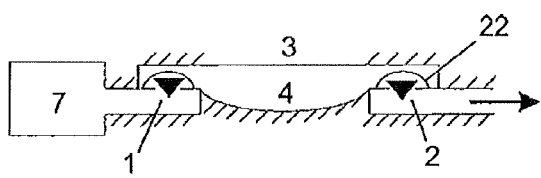
Fig.2c
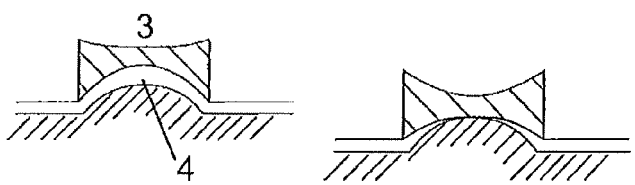
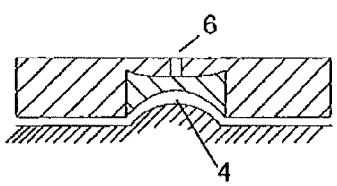
Fig.3a  Fig.3b  Fig.3c

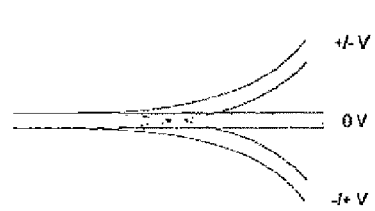
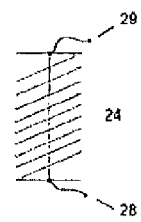
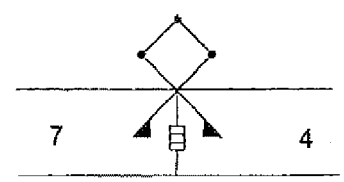
Fig.4a  Fig.4b  Fig.4c
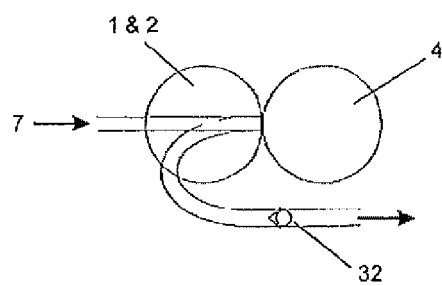
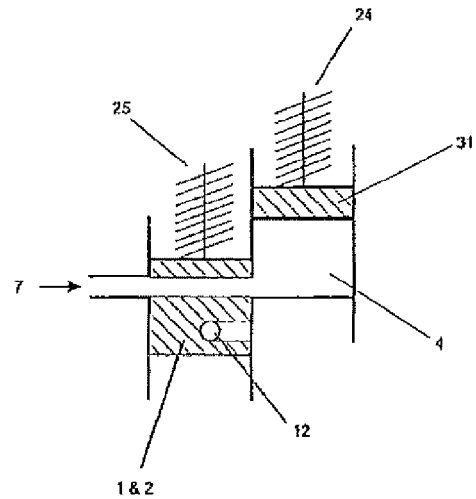
Fig.4d  Fig.4e
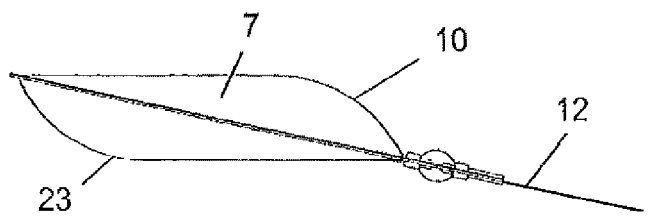
Fig.5a
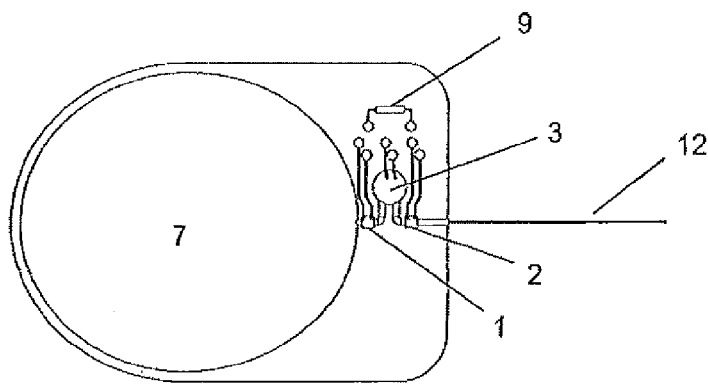
Fig.5b

INFUSION PUMP

CROSS-REFERENCE TO RELATED APPLICATIONS

This application claims priority to Greek Application No. 20090100384, filed Jul. 8, 2009, the entirety of which is hereby incorporated by reference.

1. Field of the Invention

The present invention relates to a disposable pump for infusion in general, and for insulin infusion in particular, comprising an electronic part that controls the infusion and wired or wireless communications, a power source, a medicament bag and a pumping diaphragm mechanism.

2. Background of the Invention

Insulin pumps are known in the art for regulating glucose levels in diabetics, generally of the syringe type, wherein the syringe or the entire pump may be disposable. These pumps are of relatively large size and weight, and it is difficult to fill the syringe and to mount it in the pump for safe infusion.

In the prior art, mainly linear peristaltic pumps with a medicament bag and an elastic tubing, that is kneaded peristaltically by a mechanism located on the pump, are known. Pumping mechanisms located on the disposable part of large bedside pumps are also known in the art. All these combinations have the disadvantage of less accurate infusion compared to syringe-type pumps, whereas they are not suitable for insulin infusion.

Insulin pumps and glucose meters have usually limited communication means and, as a result, the patient cannot be helped by emergency services in cases of hypoglycemia-hyperglycemia.

In the prior art, insulin pumps are mostly syringe drivers with a disposable syringe (cf. U.S. Pat. No. 6,659,980 A), or an entire pump (cf. U.S. Pat. No. 7,144,384 A). U.S. Pat. No. 6,699,218 A and U.S. Pat. No. 7,144,384 A disclose a disposable pump in which the mechanism and the needle are in the disposable part.

Syringes and piston pumps face the problem of tightness of the seal between the drug container/cylinder and the piston, and leaks have been reported by patients. From the prior art, there are known pump mechanisms with electrically transformable electroactive polymer of the tube type (cf. U.S. Pat. No. 7,307,166 A, U.S. Pat. No. 7,353,747 A, U.S. Pat. No. 7,371,223 A), of the syringe type (cf. JP 2007 127086A), and of the membrane type (cf. WO 2008 079440 A and U.S. Pat. No. 6,960,864 A).

In the communication of the pumps with a central server there exist telemedicine systems using local, short range (personal or body area networks) and remote GSM/CPRS networks (cf. U.S. Pat. No. 7,161,484 A) for informing the patient, the physician and other treatment agents via mobile phones or PDA or web pages.

The device of U.S. Pat. No. 6,960,864 A uses passive downflow valves of the same direction. However, there is a possibility of simultaneous opening in the event of overpressure from the intake. So, a pump of this type cannot be used for insulin infusion due to the danger of severe hypoglycemia and thus death of the patient.

SUMMARY OF THE INVENTION

An object of the present invention is to provide a novel small-sized, lightweight, high infusion precision and safe pump, that is simple in construction and has increased communication capabilities, thus functioning as an artificial pancreas through communication or a built-in system for measuring blood glucose.

The aforementioned and other objects are achieved by the subject matter of claim.

In the prior art, there are known diaphragm pumps with a piezoelectric membrane. The piezoelectric pumps need a special functioning frequency during which the infusion precision is acceptable. However, for small-step operation (short infusions and long pauses) as required for insulin pumps, the transition period from and to resonance, and a stable oscillation is unpredictable, both during acceleration and deceleration. That is, for a micro infusion pulse comprising a small number of septum oscillations, there is an increasing and decreasing amplitude of oscillation in a substantial, and therefore non-negligible, part of the microdosing, resulting in unpredictable dosing. On the contrary, membranes/diaphragms made of electroactive polymer have both the required pressure for subcutaneous infusion and a stable operation even for a pulse, totally silent operation and very small consumption for a portable device and a predictable and repeatable movement, wherein low cost enables them to be part of a single-use disposable device, with negligible weight and a very simple construction. Alternatively, the actuator of the diaphragm may be a shape memory alloy wire or plate (cf. U.S. Pat. No. 7,144,384 A and U.S. Pat. No. 6,699,218 A).

The present invention deals with a disposable pump for infusion in general, and for insulin infusion in particular, comprising an electronic part that controls the infusion and wired or wireless communications, a power source, a medicament bag and a pumping diaphragm mechanism. Such a diaphragm-type pumping mechanism comprises a pressure cavity with a sealed covering of a moving membrane (diaphragm) and two valves, for intake and discharge, wherein the actuator used to move the diaphragm both in the pressure cavity and in the intake valve or, alternatively, in the discharge valve is preferably of electroactive polymer (EAP). In the literature there are references to diaphragm pumps with an electroactive polymer, such as in "Performance characteristics of a polypyrrole modified polydimethyl-siloxane (PDMS) membrane based microfluidic pump" Jung Ho, Kink Tonk Lau, Rod Shepherd, Yanzhe Wu, Gordin Wallace, Dermot Diamond Elsevier Sensors and actuators A148 2008. However, according to the present invention, the direction of the valves is such as to ensure that there is no communication between intake and discharge, i.e. to preclude any free and unpredictable drug transfer to the patient in case of an accident, resulting in an important and necessary protection for medical uses.

Alternatively, the pump can also incorporate a glucose measuring part for closed-loop infusion operation and/or the electronic means or the power source in the disposable or the non-disposable part.

Further advantageous embodiments and modifications of the present invention are defined in the dependent claims

BRIEF DESCRIPTION OF THE DRAWINGS

FIG. 1 shows a pump with an infusion mechanism and two passive valves of the same direction according to the prior art.

FIG. 2 shows three preferred embodiments of a pump with a medicament bag and infusion mechanism with two valves sealing in opposite directions and blocking through-flow of liquid under pressure.

FIG. 3 shows the movement of an alternative embodiment of a double membrane/diaphragm of electroactive polymer in an open position (FIG. 3a) and in a closed position (FIG. 3b)

and the provision of alternatively higher limits of motion of the membrane-diaphragm (FIG. 3c) and lower limits of motion of the membrane-diaphragm (FIG. 3b).

FIG. 4a shows an electroactive polymer membrane, which bends in one direction for +/− polarity of electricity or bends in the other direction for reverse polarity −/+ of electricity or is in an unbent straight position with 0 V.

FIG. 4b shows an extension spring in combination with a shape memory alloy wire for tightening.

FIG. 4c shows a valve that seals under over-pressure from the intake and opens under low pressure.

FIG. 4d shows a top view of an active piston valve selecting input or output and associated with a piston pumping cavity having only one communication hole to the valve.

FIG. 4e shows a section view of the active piston valve of FIG. 4d.

FIG. 5 shows a side view (FIG. 5a) and top view (FIG. 5b) of a disposable insulin pump with an infusion error communication resistance.

Figure 6:
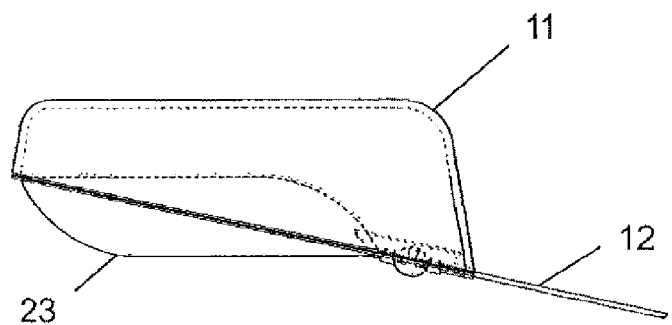

FIG. 6 shows a non-disposable infusion regulator locked on a disposable cassette, in an alternative embodiment.

Figure 7A:
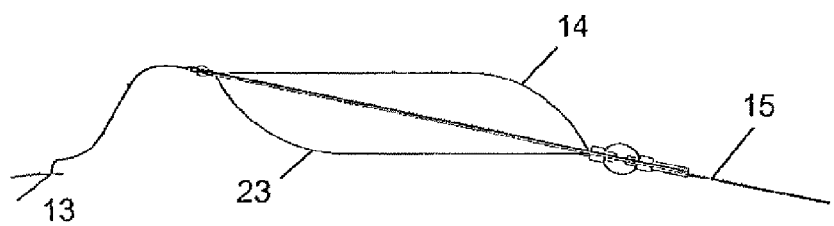
Figure 7B:
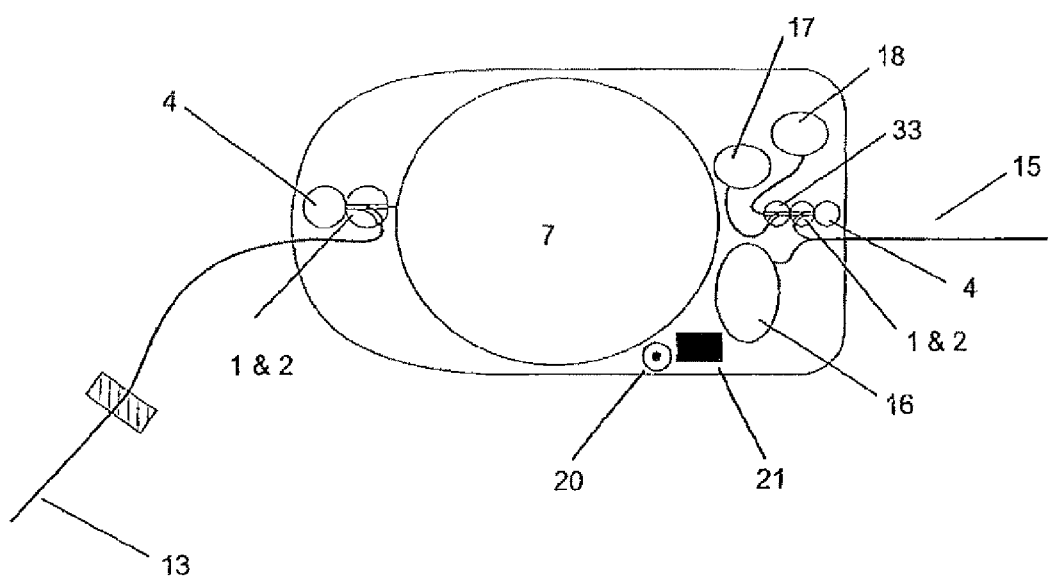

FIG. 7 shows a side view (FIG. 7a) and a top view (FIG. 7b) of an artificial pancreas including insulin bags, an insulin pumping mechanism at the left side terminating in an infusion needle/catheter, calibration and discharge liquid bags, a microflow pumping mechanism terminating in a needle/back side microdialysis circuit at the right side, an electronic infusion regulator/glucose meter chip and a zinc-air battery.

DESCRIPTION OF PREFERRED EMBODIMENTS

FIG. 1 shows a conventional insulin pump according to U.S. Pat. No. 6,960,864 A which uses passive downflow valves 1, 2 of the same direction. However, there is a possibility of simultaneous opening in the event of overpressure from the intake. So, a pump of this type cannot be used for insulin infusion due to the danger of severe hypoglycemia and thus death of the patient.

The difficulty in the design of an insulin pump lies in its realization in the smallest size possible and with the greatest possible accuracy of infusion and outmost safety.

The infusion with prior art pumps is generally of the micro-step type with progressive intermittent movement of a syringe piston by means of partial rotation of a worm screw. This type of infusion is imposed by the extremely small flow, 3 ml per week, needed for insulin infusion. In a preferred embodiment of the present invention, the injected volume for each movement of the pressure membrane is a few tenths of a microliter, equal or less than the micro-step infusion of syringe pumps. A small volume means shorter intervals between the infusion steps and better flow quality.

The insulin infusion pump of the present invention for controlling blood glucose levels in diabetics is of the diaphragm type and uses (FIG. 2) an infusion mechanism with pressure cavity 4 covered by a movable membrane-diaphragm 3 or 31 combined with intake 1 and discharge 2 valves, wherein said diaphragm is preferably moved by an electroactive polymer (EAP) (cf. U.S. Pat. No. 6,762,210 A) for noiseless and low power consumption pumping. Alternatively, the movement of the diaphragm can be effected by means of a shape memory alloy wire which is extended (wound up) by a spring and is retracted by an electric excitation, as shown in FIG. 4b, and is embodied in the pump of FIG. 2b on one hand in applying pressure 24 and, on the other hand, in the valve 25 with electric excitations 26-29. Simple springs are shown here for simplicity, but a more compact design is achieved by memory alloy wire actuators in a clam shell configuration i.e. a shape memory alloy wire at the back of a rotating actuator with extension spring in the rotation axle or over the actuation lever, as known in the art and a publication from Dynaloy Inc. for Flexinol® wire. Alternatively, a shape memory alloy plate or spring plate lamination could also be used, instead of the coil spring and wire in an adjusting curvature configuration. In principle, the pressure cavity 4 is of any shape, but is preferably a spherical or cylindrical sector for better maintenance of the nominal dimensions under pressure, or internal or external deformation, a fact that is important for the precision of the dosing. The movable part of said pressure cavity 4 can be of hard plastic 31 with flexible circumferential segments 30, as shown in FIG. 2b, for higher dose accuracy due to the repeatability of the volume in its upper and lower positions. The movement of the diaphragm 31 is effected by a voltage at the ends of the shape memory alloy wire 28, 29 and a reaction/winding up from the spring 24. The valves, active or passive, can be of any design, in particular of standard sphere, as shown in FIG. 2b, or umbrella-type such as those commercially available from company Minivalve, as shown in FIGS. 2a and c.

Said membrane-diaphragm 3 or 31 can be, in an alternative embodiment, a combination of two EAP membranes with a rubber intermediate, shaped in opposing spheroids as in a biconcave lens (as shown in the upper position in FIG. 3a), wherein a voltage of a certain polarity stretches one surface and the reversal of the polarity of this same voltage stretches the other surface in an almost flat shape, moving the diaphragm up (FIG. 3a) and down (FIG. 3b). The membranes can be commercially available and can be affixed one to the upper and the other to the lower face of the rubber intermediate, or a deposit of electrically conducting material, such as carbon ink or carbon nanofibers, can be conducted, followed by the electrochemical deposit of polypyrrole (pyrrole polymerization in a low temperature solution under constant current for a few hours) as known in the prior art. On the lower side, a deposit of a biocompatible, flexible isolating film, such as silicone, is effected.

In another preferred embodiment as shown in FIGS. 3b and c, the cavity 4 has upper and lower limits, wherein the upper limit (FIG. 3c) is just below the resting point of the membrane for no voltage (0 V) and the lower limit (FIG. 3b) of the spherical segment is above the extension limit of the membrane under voltage (usually 1-2V). In this manner, the repeatability of the movement limits of the membrane and always the same enclosed volume or volume per operating cycle is ensured. The upper hard limit has a vent 6 for the free movement of air above the membrane and the lower limit-cavity has a texture, such that any residual liquid in the cavity with the membrane under pressure is not entrapped in infinitesimal volumes, but is smoothly drained towards the exit.

In contrast to the prior art, in order to achieve the necessary safety for medical uses, the intake and discharge valves of the present invention are not of the same direction. They do not both open under pressure from the inlet or reduced pressure at the outlet; instead, they open in the opposite direction from one another, in order to block, under a passive operation without voltage, the uncontrollable flow of drug in any direction.

In a preferred embodiment as shown in FIGS. 2a and b, the discharge valve 2 can be passive or active and is provided to operate in downstream direction, that is it opens by an over-pressure in the cavity 4 and preferably above a limit of 10 kPa, such as an anti-siphon valve, and closes under pressure from the outlet. For the anti-siphon pressure, there may additionally exist a pressure rubber membrane or spring 5, as is known in the art for anti-siphon valves. However, the intake valve 1 is always active, and is provided to operate in upstream direction, as shown in FIGS. 2*a* and *b*, i.e. in passive operation it closes under pressure from the inlet (the medicament bag 7). Therefore, it can't automatically open at rest in the absence of voltage and with low suction pressure in the cavity 4 or an accidental pressure in the bag 7 as in the prior art, but must be active in order to open at intake cycle and to be able to withstand the maximum pressure in the pressure cavity 4. This valve can be activated by the EAP membrane (cf. FIG. 2*a-c*) or the shape memory alloy wire 24 (cf. FIG. 2*b*). In the case of an electroactive polymer membrane, there are two driving polarities according to FIG. 4*a*, wherein in the absence of voltage the valve is closed and closes passively even more under pressure in the inlet, one polarity +/− closes it, resisting the pressure from the main membrane without displacement, and the inverse polarity −/+ opens the valve. In the case of activation of the valve with a shape memory alloy wire, as shown in FIG. 2*b*, the spring 25 must have the required passive capacity to close the inlet under the maximum operating/infusion pressure of the diaphragm, and, under voltage across the alloy 26, 27, must contract and open the valve for the intake phase. Another embodiment may use custom active valves or commercially available active valves from Bartels Mikrotechnik, Germany, which are provided with microfilters.

In another preferred embodiment, the valves have reversed directions compared with the preceding case, as shown in FIG. 2*c*. That is, the intake valve 1 opens under pressure from input and the discharge valve 2 opens under pressure from output, and in this case, it is necessarily that discharge valve is active and opens actively during the cavity 4 overpressure phase.

Another preferred embodiment safe but using passive valves in both sides, is similar to that of FIG. 2*e-b*, but uses a passive dual simultaneous valve as shown in FIG. 4*c*, at the intake valve 1, which closes under pressure from the inlet/bag (action on reservoir side) for the required safety and opens with lower pressure in the cavity 4 (action on intake of pressure cavity side), and, in this case, the safety anti-siphon pressure is necessary in both valves 1,2.

The pressure that the active diaphragm 3 can exert is higher than the necessary 80 kPa subcutaneous infusion pressure. In the case of an electroactive polymer, it can be used an electroactive polymer layer thicker than usual, or multiple layers, or a two membrane biconcave configuration (cf. FIG. 3), or a configuration of two reversed cones joined at their apices (cf. U.S. Pat. No. 7,521,840 A) where the rubber layer is made in such a way that its downstream pressure in the infusion cycle is added to the pressure due to the stretching of the lower membrane, while the totality of the pressure of the upper membrane lifts the rubber, since the energy required for the suction is minimal. The activation of the valve(s) 1, 2 and of the pressure membrane 3 may be effected sequentially, an alternation at a time, in order to eliminate the possibility of leakage between inlet and outlet.

In an alternative preferred embodiment, a piston active valve as shown in FIGS. 4*d* and *e* can be used instead of the two valves, wherein such a piston active valve with two internal tubings at different levels, while intake and discharge holes are at same level, has two or three working positions while moving up or down. In one of these working positions a pump reservoir or medicament bag 7 is linked with a pumping cavity 4 input/output hole, while blocking the discharge link. In another one of these working positions the pump output is linked to a patient via the needle 12, while blocking the input link. In a still another of these working positions being optional both the input and the output are blocked. An advantage of this embodiment is that no communication between input and output is possible and, thus, safety is guaranteed. Alternatively, the piston can have one internal tubing while intake and discharge holes are in different levels, connecting one link at one height level and another link at another height level while moving up or down. These links are arranged in the same vertical plane forming two parallel tubings, or comprises two vertical tubing holes being offset from each other by 90 deg. and forming 90 deg. link tubes, as shown in FIGS. 4*d* and *e*. Another preferred embodiment combines the intake valve 1 and the discharge valve 2 valves with a common actuator, in a way that when a valve is open, the other is closed and vice-versa, with intermediate transition where both are closed.

An actuator can be EAP, or a shape memory alloy (Nitinol, Flexinol or other) with the extension spring, cam and follower etc. Associated with this valve, the pumping stage can be either of micro-diaphragm type which has the advantage of zero leakage and friction, or of micro-piston type (FIGS. 4*d* and *e*) which has the advantage of precision under high pressure, wherein the actuation type is the same as with the piston valve.

As an example, a preferred sequence of actions for an infusion step in the embodiment of FIG. 2*a* is described as follows:

Rest—void between steps, zero consumption (0 V valve 1 closed & 0 V pressure membrane 3 at rest—open at the upper limit), no liquid transport and cavity 4 full.

Infusion cycle for the EAP diaphragm case:

Step 1: (2V valve 1 closes under pressure & 0 V pressure membrane 3 at rest) for 0.3 sec, inlet closed with cavity 4 full.

Step 2: (2V valve 1 closed & 2 V pressure membrane 3, downward displacement-pressure and automatic opening of discharge valve 2) for 0.5 sec elementary volume infusion.

Step 3: (−2V valve 1 opens & 2 V pressure membrane 3 at the lower limit) for 0.3 sec.

Step 4: (−2V valve 1 open & 0 V pressure membrane 3 displaced to the upper limit) for 0.5 sec suction at the inlet, and return to rest with 0 V valve 1 closed without pressure, the elementary quantity infusion cycle is complete.

An advantage of the present invention lies in the patient's protection from an accidental opening of the valves 1, 2 due to an accidental pressure increase in the medicament bag/inlet, or a suction-lower siphon pressure at the discharge valve 2. The passive valves in the same direction encountered in the prior art do not protect the infusion from accidents which, in the case of diabetics with insulin infusion, are injurious.

The whole disposable device has a medicament bag 7, preferably prefilled, which is in fluid communication with the above described infusion mechanism and with the intake valve 1, and has a needle 12 in fluid communication with the discharge valve, or alternatively a microneedle network, as is known in the prior art, for direct subcutaneous infusion, or alternatively a catheter with a needle at its end 13. The disposable part comprises a self-adhesive at its lower part 23 for adhesion to the body and a connector for fastening at its upper part of the non-disposable electronic infusion regulator 11 (FIG. 6) in such a way that the two together are adhered to the skin. The infusion regulator 11 has electrically conductive contacts, corresponding to those of the disposable part 10 for power transfer and flow regulation and pressure measurement. For this reason the disposable part may have thick or thin film conductive material lanes extending from the electroactive polymers to the contacts. These lanes can also be made using silk screen or other printing techniques with conductive inks.

The infusion may preferably be digital-microstep, by injecting, at calculated time intervals for each infusion rate, in the case of insulin infusion, the same elementary quantity of the order of 1-5 tenths of a microliter, equal to the volume of the cavity 4. The accuracy of this elementary volume, especially in the case of the embodiment of FIG. 3c with upper and lower limits, is decisive for the overall accuracy and is achieved with a micro-mold and a corresponding micromolding method ensuring to the infusion molded plastic a dimensional accuracy better than 10 µm.

The cavity 4 may also be of larger size and, since the electroactive polymers have an excellent linearity of displacement versus applied voltage, they may operate under analog voltage but intermittently with elementary infusion quantities, as follows: Closing the intake valve 1, increase of the infusion membrane voltage ΔV for elementary quantity infusion, then 0 V at the infusion membrane 3 and then 0 V at the intake valve 1 (therefore it does not open on suction from the infusion membrane 3) which tries to return at the upper position, but can't achieve that since both valves 1, 2 close by a lower pressure at the middle, and therefore remains at the same position at rest. At the next cycle, the voltage is increased similarly by ΔV up to the maximum voltage (2V), whenever the described 4 step cycle is followed. This microstep technique enables, with small changes of the pressure membrane voltage, to achieve extremely small infusion quantities per step. The analog voltage at the membrane may, in another preferred embodiment, come from a conventional potentiostat for a better control of the position of the membrane.

The occlusion alarm pressure measurement, as a general rule of the order of 80 kPa, is preferably effected from feedback of the electroactive polymers or the memory alloy wires themselves, or by a pressure sensor at the infusion regulator, in contact with the hydraulic discharge system. In a subcutaneous infusion, where the accuracy of the maximum infusion pressure need not be high, the pressure may be controlled by the maximum force of the actuator and, in this case, it is necessary to detect the displacement of the diaphragm 3 or 31 at its two extreme positions, which can be achieved whether by said feedback of actuators themselves (measuring their electrical parameters) or using low-cost optical means or an electric contact (signal up and signal down). In the occlusion pressure determination, time to this full travel is also taken into account.

The present invention may also be applied to general purpose and larger injected volume disposable pumps, in cases of pain control, chemotherapy, parenteral feeding, enteral feeding, etc., and in this case the pressure measurement at the diaphragm/membrane could inform, in addition to the downstream occlusion pressure, about an absence of liquid or an upstream occlusion and the presence of air in the system (air bubble detection), as mentioned in U.S. Pat. No. 5,980,490 A, which is briefly described bellow: If the pressure membrane is pressed, with both valves closed, in which case both must be active, if inside the cavity 4 only liquid is present, the membrane will not be displaced, since liquids are incompressible, and the pressure will increase excessively. If air is present, the pressure will increase less than before, and the membrane will be displaced. If there is no liquid in the inlet (upstream occlusion), the membrane will remain at the lower point without suction and without pressure increase. If there is a leakage through an eventual hole, or a non-welded membrane or a bad valve, air will appear in the system as risk factor and leakage will behave as air in line letting diaphragm go down.

A further advantage of the present invention lies in the ability to calibrate any disposable device as to its accuracy. It is known to calibrate the measuring photodiode of pulse oximeters using a resistor connected to the disposable finger clip. According to the present invention, the infused volume per stroke is measured during production and, according to a preferred embodiment, a thick film control resistor 9 is cut near the contacts with the electronic part, using laser trimming as known in the industrial practice, such that the mechanical constant of volume/infusion cycle by means of which the infusion rate is calculated is not constant for the computer in the electronic part, but a parameter changing according to the reading of said resistance or by means of another digital communication method on every disposable part and, in this way, a corrected infusion error of 0% is achieved. Because the production quantities of the disposable insulin pumps are large, the production is generally fully automatic, and the above adjustment is compatible for such a production without increasing the costs of the disposable device. The dose accuracy is important for a pump that may be part of a closed infusion loop in conjunction with a blood glucose measuring system and with corresponding algorithms contained in the electronic part (cf. reference numeral "11" in FIG. 6 or "21" in FIG. 7).

In another preferred embodiment of the present invention, the disposable part 14 includes the electronic drive 21 and the glucose meter as described above. Instead of non-disposable driving electronics fastening to the disposable part, as shown in the upper part of FIG. 6, a power source 20 plus measuring and driving electronics and communications which may be combined in a unique chip 21 on the disposable part which thus becomes a complete pump or an artificial pancreas. The power source 20 may be a paper battery, either of the newer technology with nanomaterials, or a conventional device or button-type zinc-air batteries like those used for hearing aids.

In more detail, the present invention may be combined with the teaching of GR20090100135 and constitute a unique CGMS (continuous glucose measurement system) and infusion assembly, under a unique envelop, with two needles, one for infusion 13 and one for measuring 15 with auto-calibration as shown in FIG. 7. In this case there is a single disposable part with two pumps, one for insulin infusion (parts 1, 2, 3) and microflow (33,1&2,4) and four containers, three for measuring (glucose 18, physiological serum 17, waste 16) and one for insulin infusion 7 as particularly shown in FIG. 7b. In this particular embodiment, the measurement needle 15 is preferably inserted at an angle to the subcutaneous tissue in the proximity of the device, while the infusion takes place with a catheter a few centimetres further (usually 7 cm), as far as needed to avoid a diffusive interference between the two sites, which could alter the measurement. There are presently commercially available applications with an independent pump and continuous measuring device (CGMS), with two needles spaced apart from each other.

So, FIGS. 7a and b show a single integrated consumable assembly including two pumps, wherein one of these pumps is provided for infusion of insulin shown here as a preferred embodiment and comprises a piston valve as shown in FIGS. 4d and e and the cavity 4, whereas the other pump is a microfluidic pump of the same valve type used as a selection valve 33 for reservoirs 17 and 18 and followed by an inlet/discharge valve 1&2 for the cavity 4. So, the consumable assembly has four reservoirs, a first reservoir 7 for insulin, a second reservoir 18 for glucose or high glucose concentration, a third reservoir 17 for saline or low glucose concentration, and a fourth reservoir 16 for waste.

In the case of venous infusion (use in ICU), the infusion catheter coincides with the measuring catheter as follows: It has 3 lumens, two for the closed microdialysis and calibration loop and one open ended lumen for insulin infusion, as far as the blood flow isolates the infusion from the measurement. The 3 measuring electrodes are situated inside the outer catheter envelop, as in our above mentioned patent, with inverse (from behind) microdialysis communication with auto calibration. For venous infusions, the enzyme catheter can be coated with an additional biocompatible film, to reduce diffusion to and from the circulating blood, in such a way that the auto-calibration with reverse microdialysis can function correctly.

Alternatively, there may be a third pump and a corresponding fourth lumen for corrective glucose infusion, in cases of confirmed hypoglycemia.

The electronic part may be a processor with built-in personal network range radio-communications transmitter-receiver. Such an all-in-one silicon processor system 21, with an analog-to-digital converter and two potentiostats, for the electrical glucose measurement and the micro-step membrane displacement 3, is the Texas Instruments CC981H Sensium™, especially for adhesive sensors. The preferred manufacturing process for the present invention is the so-called chip on board technology. This processor can directly drive the electroactive polymers and measure glucose levels in the subcutaneous tissue with its built-in potentiostat part. Programming of the infusion protocol is effected through a hand-held communicator with radio connection, operated by the user, which provides all alarms and the required communicating means to the user. Prior to placing this artificial pancreas on the body with the two needles as above mentioned, the user transfers, through (serial wired) contact of the two devices, the codes and the serial numbers of the one apparatus to the other, for a point to point secure communication. He securely programs the pump with the secure open-loop infusion protocol and the closed loop levels to be used. Thereafter, the artificial pancreas may be adhered with the self-adhesive tape 23 to the body, as it is very lightweight and small-sized, with the two needles in a safe distance. The hand-held communicator monitors and records the infusion, notifies the user, and transmits data to the pump as described below. In this embodiment, wherein the infusion regulator is situated on the disposable part, the measured mechanical constant (infusion steps per ml) or the infusion error of the particular pump may be stored in the said infusion regulator's microprocessor memory.

Insulin is known to precipitate in long contact with incompatible materials, or through badly designed flow paths. The complete disposable device may consist of layers of an insulin compatible plastic such as cyclic polyolefin, using preferably a micromolding method for dimensional accuracy and has at its end the bag and cavities, inside which the electroactive polymers (EAP) and the flexible parts of the valves are placed, and the layers are plasma treated and sealed. Alternatively, at the lower part a hard or semi-hard plastic can be used, with molded rubber or film on top, e.g. silicone or bromobutil rubber or polyolefin film, with all the necessary upper cavities and conformations (half pipes etc.). The pre-filling insulin amount, generally 3 ml, is inserted in said bag through a circumferential lumen which is itself sealed after filling using an analogous method.

The lower part of said disposable insulin bag may be made in the form of a cassette, which forms a single compact assembly with the non-disposable electronic part, once the latter is secured on the former. Alternatively, both parts may be made semi-hard, with the electronics printed-circuit card made of a flexible material, for the convenience of the patient.

The extremely small dimensions of said infusion microvolume result in the semi-hard plastic of the construct to be locally hard with a constant, non-deformable volume during infusion, while at the larger dimensions of the bag, it is soft and is uniformly emptied by the pumping vacuum, which is also controlled by the material's thickness, which is smaller at the upper part and larger at the lower part of the bag. In addition, the medicament bag is textured, at least in one side, to help emptying, i.e. it to prevent the upper membrane to stick to the lower one and thus block emptying, since the texture drains easily the liquid towards the infusion mechanism.

The pre-filling of the bag with insulin is preferably effected by using filters which extract the air from the injected drug, and thus an air bubble detector is not needed for this reason, and also because, when the infusion is subcutaneous, there is no embolism danger for the patient in case of air infusion in the area.

In the case of a non-prefilled bag, the bag's cassette may comprise a hole or holes covered by a hydrophobic, watertight but air-permeable material to help sterilizing the disposable device using ethylene oxide, which penetrates the hydrophobic membrane and thus, sterilization by using gamma rays is avoided. In this case, filling of the bag with medicament may be effected through the rubber gasket which is pierced be a filling needle.

Alternatively, the means for retaining the disposable-infusion regulator pair on the body may be a belt at the waist or elsewhere, and in this case the needle is guided by a catheter tubing to the infusion point.

The power source for driving the infusion pump, in the case of a non-disposable infusion regulator 11, comprises a battery, preferably rechargeable by low-frequency short range electric fields or by a contactless magnetic link, or a rechargeable pocket battery pack with charging cable, electronic circuits providing the safety of EN60601-1 and EN60601-2-24 standards, timing and drug pressure measuring devices at the outlet, short range wireless communications means with minimal power consumption, with a usual range not more than 5 meters. In order to confirm important commands, and the communications coupling and the password between this portable instrument with the user through communications interfaces, secondary means of optical communication IrDA may also be present, or electrical contacts which ensure secret and secure communications, as is known to the secure network experts.

The communication with the user is preferably through a portable, hand-held device, having the size of a GSM phone, and having keys, some of which may be of varying function, depending on the use (soft keys), a graphics display for displaying the programming of the pump, the protocol, the history, infusion graphs, food-calories selection, exercise input, glucose and other measured parameters graphs, decisions for closed-loop infusion and for alarm handling. It comprises electronic circuits providing the safety of EN60601-1 and EN60601-2-24 standards as part of the pump, but at a distance, which translate the programming to commands and units understood by the infusion controller. It comprises a battery, preferably of the lithium ion type, and sufficient memory capacity for all communication means. It comprises transmitters-receivers of long range GSM/GPRS and/or UMTS and/or Wi-Fi and/or Wi-Max networks, for TCP/IP communication protocol to a distant Internet server, and transmitters-receivers of short range personal area RF like Bluetooth Low Energy and/or optical IrDA and/or RS232-USB networks. Data transmissions can also be via any new wireless connection technique. The device preferably also comprises position determination with built-in GPS and triangulation position determination by means of GSM.

Using the transmitters-receivers, the user communication device is linked by the lower possible cost means (mainly Wi-Fi) to a patient monitoring server, and the corresponding data base. It receives information for the status of the devices on and near the user (e.g. external physical exercise measuring instruments, continuous glucose measurement measur by an extracorporeal or implantable sensor, tape glucose meters, ketone meters, etc.), the communications status of each device in the network, of the various batteries and the measurement results, and transmits it to the server, which records them in data bases and displays them to the Internet or to portable devices, such as a portable pump user communicator, depending on each user's needs.

The decision making is not necessarily made by the user who, in case she or he is in coma, is incapacitated, or in other cases such as with children, or with persons lacking the required capacity, and in this case the numerous communications means of the system can be of help, such as e.g. for food supply and for bolus calculation, it can be programmed by another person, such as a relative, who communicates to the server by using mobile or fixed means, and then to the pump.

In the case of a closed-loop, the decisions are made through local algorithms based on neural networks for the prediction of blood glucose (S. G. Mougiakakou, A. Prountzou, D. Iliopoulou, K S. Nikita, A. Vazeou, C. S. Bartsocas, "Neural Network based Glucose—Insulin Metabolism Models for Children with Type 1 Diabetes," Engineering in Medicine and Biology Conference 2006 (EMBO'06), IEEE, New York City, USA, September 2006) which is an estimation of the next blood glucose value corresponding to the measured subcutaneous level, and which are approximately 30 minutes apart, which prediction is used as an input to a PID algorithm for the control of the infusion (cf. U.S. Pat. No. 6,740,072 A) in combination with physiological patient's parameters, information for carbohydrate administration during meals and of exercise, each of which creates a different glucose algebraic equivalent kinetics. According to a preferred embodiment of the present invention, PID and neural network parameter correction is based on patient's statistical data and on new scientific knowledge, through the server, without the need to upgrade the pump.

In this case, a certified server according to the EN60601-1 standard is needed, or a certified part-printed card thereof.

The alarms that are necessary for the standards, as well as others provided for better servicing and error avoidance are not required to reach the patient, depending on the configuration of the pump, but rather they may be serviced by the relatives or the physician or an attending person, in case of domestic attendance. The patient's localization using GPS and the alarm reception via SMS, e-mail or automatic phone call by the life-saving means avoids any delays which could prove fatal in the case of diabetic patients. In the Internet, the pages with the state of various organ systems appear, together with a diabetes page with pump protocol graphs, an infusion graph, glucose-ketone-lactose statistical data and historical data for meals and physical exercise, a page of heart function with arrhythmias, heart pulse BPM, heart statistics, a lung page with spirometric and blood oxygen statistical data and a log of the respirator.

The closed-loop infusion may also be used in a semi-closed loop configuration. In this case, the pump automatically makes decisions within predefined limits, adjusted by the physician and the patient, depending on the training of the patient and the progress of the treatment. The pump, via the above mentioned user communications system, asks the user, in cases where it needs to inject a quantity outside the limits or where a rate of change of glucose levels which differs from the mathematically predicted one is diagnosed: In case of unexpected glucose rise "Did you take a meal which you didn't record, or larger or different from the one recorded?", or, in case of unexpected glucose lowering, "Did you have physical exercise which you didn't record or did you make an error in recording?". It then proposes a corrective dose that, if relatively small, the patient, or, if relatively large, the physician via telemetry must agree upon and validate or the consumption of sugar/candy.

I claim:

1. An infusion pump, comprising electronic infusion regulating means with wired or wireless communication means and a power source, a medicament bag and an infusion device, said infusion device being in fluid communication with said medicament bag and comprising first and second valves, a pressure cavity provided between said first and second valves and a membrane covering said cavity, wherein said infusion device comprises at least two active actuators, one of said actuators being adapted to apply pressure to said membrane for fluid displacement in said cavity, and the other of said actuators being adapted to operate said first valve which is adapted to passively close in the flow direction of a fluid from said medicament bag through the cavity, wherein the second valve is adapted to close in a direction opposite to said flow direction.

2. The infusion pump according to claim 1, wherein in case said second valve operates as an active valve, said second valve is adapted to be actuated by the same actuator as said first valve in a way that always said second valve is closed when said first valve is open.

3. The infusion pump according to claim 1, wherein said infusion regulating means is adapted to monitor an actuation travel of said one of said actuators being adapted to apply pressure to said membrane for fluid displacement in said cavity through electrical parameters of actuator changing with actuation stress/travel, as well as time of travel for safety and occlusion pressure alarm determination.

4. The infusion pump according to claim 1, wherein said infusion device with said medicament bag define a disposable part, and the electronic infusion regulating means and eventually the power source are located in a non-disposable infusion regulator which is attached to said disposable part and communicates with it via contacts for driving, infusion error reading and optionally for pressure measurement.

5. The infusion pump according to claim 4, wherein said disposable part is calibrated during production for infusion rate errors and comprises communication means for transmitting information about an error and for correcting this error by the infusion regulator.

6. The infusion pump according to claim 4, wherein said disposable part is adapted to be prefilled with a drug.

7. The infusion pump according to claim 4, wherein said disposable part comprises at least a hole covered by an hydrophobic, watertight but air-permeable material to facilitate sterilization with ethylene oxide, and by a rubber gasket for filling the medicament bag through a drug introduction needle.

8. The infusion pump according to claim 4, wherein said disposable part further comprises bags, a glucose sensor microflow calibration means, an infusion needle for insulin infusion, a measurement needle for glucose measurement, a back side microdialysis circuit being an internal part of said measurement needle, and a glucose sensor provided on an external part of said measurement needle, wherein both said needles are spaced from each other by a predetermined distance, and wherein said infusion regulator for any case self-contained operation with built-in electronics or non-disposable infusion regulator includes a memory adapted to record dosing accuracy calibration data, said power source and said wireless or wired communication means.

9. The infusion pump according to claim 8, wherein networks are provided which are used by an algorithm to predict the blood glucose concentration, and wherein said algorithm is provided to use a proportional integral derivative (PID) algorithm for infusion control.

10. The infusion pump according to claim 8, wherein a catheter is provided for intravenous administration which catheter comprises three integral lumens, one open at its end for infusion and the other two closed at their end, but communicating with a closed microflow and back side microdialysis circuit, for calibrating said glucose sensor.

11. The infusion pump according to claim 1, further comprising a handheld user communicator device including a user interface display, command input keys, communication means for data transmission from and to a central server computer via an Internet connection, or other wireless connection technique, means for local communication with said infusion regulator, sensors at a short distance from the user, and a memory for recording infusion events (event log) and optionally measurement events as communicated by said infusion regulator.

12. The infusion pump according to claim 11, wherein said handheld user communicator device is adapted to use said communication means for transmitting the infusion events and optionally the measurement events as communicated by said infusion regulator to a remote database.

13. The infusion pump according to claim 11, wherein said handheld user communicator device includes a memory for storing a food library that may be updated by said long distance communication means to remote database with the corresponding glucose equivalent units and sensor or input of exercise also translated to negative glucose equivalent, either for calculating an insulin bolus or for communicating them to an infusion and measurement system for closed-loop infusion control.

14. The infusion pump according to claim 11, wherein reports and alarms of the pump and/or a glucose meter system are transmitted from said handheld user communicator device or a central computer via text messages (SMS) or other telecommunication means to persons capable to process the data.

15. The infusion pump according to claim 1, comprising a body having a lower skin contacting side at which a self-adhesive is provided to support the weight of the pump.

16. The infusion pump according to claim 1, wherein said two valves are combined in a piston valve which is movable to at least a first working position and a second working position and adapted so that in said first working position said medicament bag is linked with said cavity while blocking an output, and in said second working position said cavity is linked with said output while blocking the link with said medicament bag.

17. The infusion pump according to claim 16, wherein said piston valve is movable to a third working position in which both the links with said medicament bag and said output are blocked.

18. An infusion pump consumable or consumable infusion pump according to claim 1, wherein the infusion pump is carrying individual infusion accuracy calibrating data, and the calibration is done during manufacturing/quality inspection of said infusion pump consumable or consumable infusion pump.

19. The infusion pump according to claim 8, wherein said infusion regulator is adapted to operate in accordance with an algorithm for a closed-loop insulin infusion control in relation to the measured glucose, physiological parameters, carbohydrate ingestion and physical exercise information.

20. The infusion pump according to claim 10, wherein said glucose sensor comprises a diffusion reducing cover in both flow directions.

* * * * *